US00PP19145P2

(12) United States Plant Patent

Mehring-Lemper

(10) Patent No.: US PP19,145 P2

(45) Date of Patent: Aug. 26, 2008

(54) *AGASTACHE* PLANT NAMED 'AGA 404'

(50) Latin Name: *Agastache hybrida*
Varietal Denomination: AGA 404

(75) Inventor: Manfred Mehring-Lemper, Hann. Münden (DE)

(73) Assignee: Ernst Benary Samen Zucht GmbH., Hann. Münden (DE)

( * ) Notice: Subject to any disclaimer, the term of this patent is extended or adjusted under 35 U.S.C. 154(b) by 0 days.

(21) Appl. No.: 11/801,675

(22) Filed: May 9, 2007

(51) Int. Cl.
*A01H 5/00* (2006.01)

(52) U.S. Cl. ..... Plt./399

(58) Field of Classification Search ..... Plt./399, Plt./263

See application file for complete search history.

*Primary Examiner*—Annette H Para
*Assistant Examiner*—S. B. McCormick-Ewoldt
(74) *Attorney, Agent, or Firm*—C. A. Whealy

(57) ABSTRACT

A new and distinct cultivar of *Agastache* plant named 'AGA 404', characterized by its compact, upright, outwardly spreading and open plant habit; freely branching habit; relatively large and dense inflorescences with small violet-colored flowers; freely and continuous flowering habit; and good garden performance.

1 Drawing Sheet

Botanical designation: *Agastache hybrida.*
Cultivar denomination: 'AGA 404'.

BACKGROUND OF THE INVENTION

The present invention relates to a new and distinct cultivar of *Agastache,* botanically known as *Agastache hybrida* and hereinafter referred to by the same 'AGA 404'.

The new *Agastache* is a product of a planned breeding program conducted by the Inventor in Hann. Münden, Germany. The objective of the breeding program was to create new *Agastache* cultivars with large and dense inflorescences and attractive flower coloration.

The new *Agastache* originated from an open-pollination during the summer of 2003 in Hann. Münden, Germany, of an unnamed selection of *Agastache hybrida,* not patented, as the female, or seed, parent with an unknown selection of *Agastache hybrida* as the male, or pollen, parent. The new *Agastache* was discovered and selected by the Inventor as a single flowering plant within the progeny of the stated open-pollination in a controlled environment in Hann. Münden, Germany during the summer of 2004.

Asexual reproduction of the new *Agastache* by vegetative cuttings in a controlled environment in Hann. Münden, Germany during the winter of 2004, has shown that the unique features of this new *Agastache* are stable and reproduced true to type in successive generations.

SUMMARY OF THE INVENTION

The cultivar AGA 404 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'AGA 404'. These characteristics in combination distinguish 'AGA 404' as a new and distinct cultivar of Agastache:

1. Compact, upright, outwardly spreading and open plant habit.
2. Freely branching habit.
3. Relatively large and dense inflorescences with small violet-colored flowers.
4. Freely and continuous flowering habit.
5. Good garden performance.

Compared to plants of the female parent selection, plants of the new *Agastache* are more compact and differ in flower coloration.

Plants of the new *Agastache* can also be compared to plants of the cultivar Honey Bee Blue, not patented. In side-by-side comparisons conducted in Hann. Münden, Germany, plants of the new *Agastache* and the cultivar Honey Bee Blue differed in the following characteristics:

1. Plants of the new *Agastache* had smaller leaves than plants of the cultivar Honey Bee Blue.
2. Plants of the new *Agastache* had larger inflorescences than plants of the cultivar Honey Bee Blue.
3. Plants of the new *Agastache* and the cultivar Honey Bee Blue differed in flower color.

BRIEF DESCRIPTION OF THE PHOTOGRAPHS

The accompanying colored photographs illustrate the overall appearance of the new *Agastache,* showing the colors as true as it is reasonably possible to obtain in colored reproductions of this type. Colors in the photographs may differ slightly from the color values cited in the detailed botanical description which accurately describe the colors of the new *Agastache.*

The photograph at the bottom of the sheet comprises a side perspective view of a typical flowering plant of 'AGA 404' grown in a container.

The photograph at the top of the sheet is a close-up view of typical inflorescences and inflorescence buds of 'AGA 404'.

DETAILED BOTANICAL DESCRIPTION

The aforementioned photographs and following observations, measurements and values describe plants grown in Loudon, N.H. during the winter and under commercial practice in a glass-covered greenhouse. During the production of the plants, day temperatures ranged from 20° C. to 22° C. and night temperatures ranged from 18° C. to 20° C. After planting, plants were pinched one time. Plants had been growing for about ten weeks when the photographs and description were taken. In the following description, color references are made to The Royal Horticultural Society Colour Chart, 1995 Edition, except where general terms of ordinary dictionary significance are used.

Botanical classification: *Agastache hybrida* cultivar AGA 404.

Parentage:

*Female, or seed, parent.*—Unnamed selection of *Agastache hybrida,* not patented.

*Male, or pollen, parent.*—Unknown selection of *Agastache hybrida,* not patented.

Propagation:

*Type.*—By vegetative cuttings.

*Time to initiate roots, summer.*—About 15 to 20 days at 22° C.

*Time to initiate roots, winter.*—About three to four weeks at 20° C.

*Time to produce a rooted young plant roots, summer.*—About four weeks at 20° C.

*Time to produce a rooted young plant roots, winter.*—About five weeks at 20° C.

*Root description.*—Fine, fibrous; 158C in color.

Plant description:

*Plant form/habit.*—Compact, upright, outwardly spreading and open plant habit; vigorous growth habit. Freely branching habit with about three to four lateral branches, each with several secondary branches; pinching enhances branching potential.

*Plant height.*—About 42 cm.

*Plant width (spread).*—About 27 cm.

*Lateral branches.*—Length: About 30 cm. Diameter: About 5 mm. Internode length: About 4.5 cm. Strength: Strong. Texture: Pubescent. Color: 146A.

Foliage description:

*Arrangement.*—Opposite, simple.

*Length.*—About 4.6 cm.

*Width.*—About 3.4 cm.

*Shape.*—Cordate.

*Apex.*—Acute.

*Base.*—Cordate.

*Margin.*—Crenate.

*Texture, upper surface.*—Smooth, glabrous.

*Texture, lower surface.*—Pubescent.

*Venation pattern.*—Pinnate; arcuate.

*Color.*—Developing and fully expanded leaves, upper surface: 147A; venation, 147C. Developing and fully expanded leaves, lower surface: 147B; venation, 147C.

*Petiole length.*—About 3.4 cm.

*Petiole diameter.*—About 2 mm.

*Petiole texture, upper and lower surfaces.*—Pubescent.

*Petiole color, upper surface.*—146A.

*Petiole color, lower surface.*—146B.

Flower description:

*Flower type and habit.*—Numerous single bilabiate flowers arranged in verticillasters arranged in axillary large and dense spikes; flowers sessile. Individual flowers face upright to outward. Freely flowering habit with about 300 flowers and flower buds per spike. Flowers persistent.

*Natural flowering season.*—Plants flower from late June through September in the Northern Hemisphere; flowering continuous during this period.

*Inflorescence longevity on the plant.*—About three to four weeks.

*Fragrance.*—None detected.

*Inflorescence length.*—About 6 cm to 7 cm.

*Inflorescence width.*—About 3 cm.

*Flowers.*—Appearance: Zygomorphic; bilabiate. Length: About 1.6 cm. Diameter: About 4 mm by 5 mm.

*Flower buds.*—Length: About 9 mm. Diameter: About 2.5 mm. Shape: Elongated oblong. Color: 92A.

*Corolla.*—Petal arrangement/appearance: Bilabiate; five petals, upper two petals fused and lower three petals fused, all five petals fused at base into a tubular structure. Petal length: Upper petals, lobes: About 2 mm. Lower petals, lobes: About 3 mm. Petal width: Upper petals, lobes: About 1 mm. Lower petals, lobes: About 4 mm. Petal apex: Rounded to broadly acute. Petal margin: Upper petals: Entire. Lower petals: Sinuate. Petal texture, upper and lower surfaces: Smooth, glabrous. Petal color: When opening, upper surface: 91A. When opening, lower surface: 91B. Fully opened, upper surface: 92B to 92C; color becoming closer to 97B with development. Fully opened, lower surface: 92B; color becoming closer to 92C with development.

*Calyx.*—Quantity/arrangement: One single calyx tube per flower; five fused sepals. Length: About 2 mm. Diameter: About 1 mm. Shape: Lanceolate. Apex: Acute. Margin: Entire. Texture, upper surface: Smooth, glabrous. Texture, lower surface: Pubescent. Color, upper surface: 148D. Color, lower surface: Towards the apex, 94C; fused portion, 147C to 147D.

*Peduncles.*—Length: About 3.5 cm. Diameter: About 2 mm. Strength: Strong. Angle: Erect to about 45° from vertical. Texture: Pubescent. Color: 146B.

*Reproductive organs.*—Stamens: Quantity per flower: Four. Filament length: About 5 mm. Filament color: 92B. Anther shape: Rounded. Anther length: About 1 mm. Anther color: 92A. Pollen amount: Scarce. Pollen color: 202D. Pistils: Quantity per flower: One. Pistil length: About 1.6 cm. Style length: About 1.4 mm. Style color: 92C. Stigma shape: Bi-parted. Stigma color: 92A. Ovary color: 145A.

*Seed/fruit.*—Seed nor fruit production has not been observed.

Disease/pest resistance: Plants of the new *Agastache* have not been noted to be resistant to pathogens or pests common to *Agastache.*

Garden performance: Plants of the new *Agastache* have been observed to have good garden performance and to be tolerant to rain, wind and temperatures ranging from about 0° C. to 38° C.

It is claimed:

1. A new and distinct *Agastache* plant named 'AGA 404' as illustrated and described.

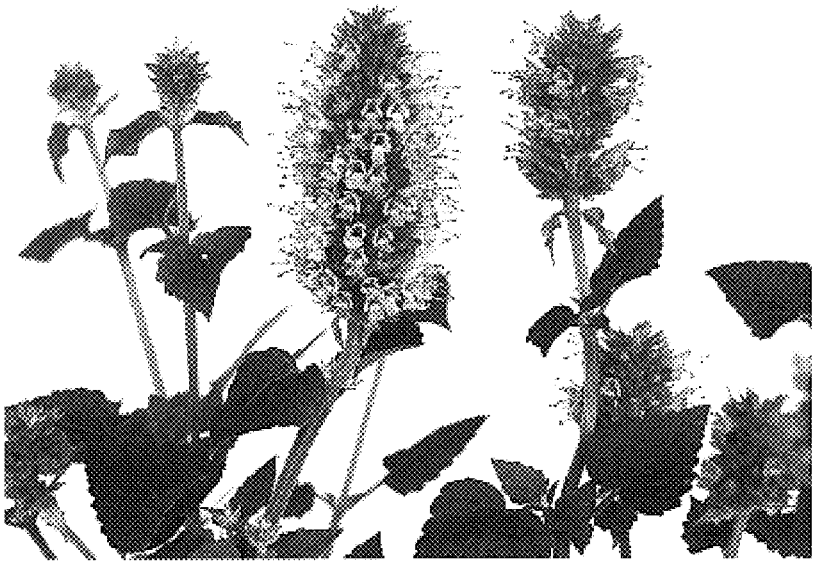
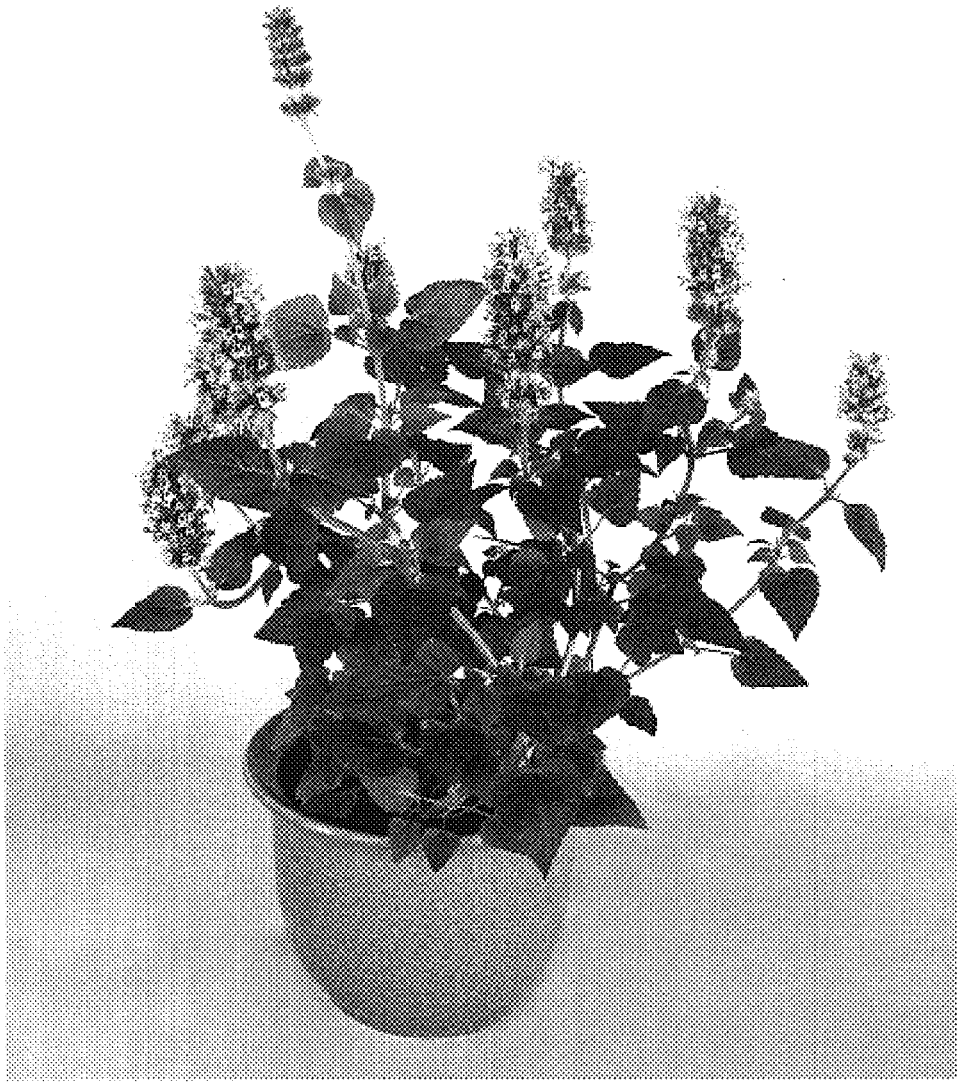

* * * * *